US011287377B2

(12) United States Patent
Hou-Broutin et al.

(10) Patent No.: US 11,287,377 B2
(45) Date of Patent: Mar. 29, 2022

(54) DETECTION SYSTEM FOR AN ELECTRONIC NOSE AND AN ELECTRONIC NOSE COMPRISING SUCH A SYSTEM

(71) Applicants: ARYBALLE, Grenoble (FR); COMMISSARIAT A L'ENERGIE ATOMIQUE ET AUX ENERGIES ALTERNATIVES, Paris (FR); UNIVERSITÉ GRENOBLE ALPES, Saint-Martin-d'Heres (FR); CENTRE NATIONAL DE LA RECHERCHE SCIENTIFIQUE, Paris (FR)

(72) Inventors: Yanxia Hou-Broutin, Bilieu (FR); Sophie Brenet, Grenoble (FR); Thierry Livache, Jarrie (FR); Cyril Herrier, Grenoble (FR); Tristan Rousselle, Grenoble (FR)

(73) Assignees: ARYBALLE, Grenoble (FR); COMMISSARIAT A L'ENERGIE ATOMIQUE ET AUX ENERGIES ALTERNATIVES, Paris (FR); UNIVERSITÉ GRENOBLE ALPES, Saint-Martin-d'Heres (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 42 days.

(21) Appl. No.: 16/647,414

(22) PCT Filed: Sep. 11, 2018

(86) PCT No.: PCT/FR2018/052219
§ 371 (c)(1),
(2) Date: Mar. 13, 2020

(87) PCT Pub. No.: WO2019/053366
PCT Pub. Date: Mar. 21, 2019

(65) Prior Publication Data
US 2020/0256793 A1 Aug. 13, 2020

(30) Foreign Application Priority Data

Sep. 14, 2017 (FR) .................................. 1758547

(51) Int. Cl.
*G01N 21/552* (2014.01)
*G01N 21/77* (2006.01)
*G01N 33/00* (2006.01)

(52) U.S. Cl.
CPC ........... *G01N 21/553* (2013.01); *G01N 21/77* (2013.01); *G01N 33/0031* (2013.01); *G01N 2021/7793* (2013.01)

(58) Field of Classification Search
CPC .. G01N 21/553; G01N 21/77; G01N 33/0031; G01N 2021/7793; G01N 33/007; G01N 21/7703
See application file for complete search history.

(56) References Cited

U.S. PATENT DOCUMENTS 5,152,287 A * 10/1992 Kane .................... A61B 5/1459
600/364
6,085,576 A * 7/2000 Sunshine ........... G01N 33/0031
73/29.01

(Continued)

FOREIGN PATENT DOCUMENTS

EP 3185011 A1 6/2017

OTHER PUBLICATIONS

Brenet et al.,"Development of a Novel Multiplexed Optoelectronic Nose for Analysis of Volatile Organic Compounds," ISOCS/IEEE International Symposium on Olfaction and Electronic Nose (ISOEN), IEEE, May 2017, pp. 1-3.

(Continued)

*Primary Examiner* — Samuel P Siefke
*Assistant Examiner* — Henry H Nguyen
(74) *Attorney, Agent, or Firm* — Arent Fox LLP

(57) ABSTRACT

The invention relates to a detection system for an electronic nose capable of detecting and identifying a set of com- (Continued)

pounds that can be found in a gaseous sample, the detection system comprises a plurality of cross-reactivity detection sensors (D1, D2, D3, D4, D5, D6, D7) for supplying signals representing the presence of one or more compounds of said set in the gaseous sample, and which is particularly characterised in that the detection system further comprises at least one reference sensor (RI) for supplying a signal representing the measurement noise of the detection system. The detection system further relates to an electronic nose comprising such a detection system.

21 Claims, 11 Drawing Sheets

(56) References Cited

U.S. PATENT DOCUMENTS

| | | | | |
|---|---|---|---|---|
| 2006/0141527 | A1* | 6/2006 | Caracci | G01N 21/7743 435/7.1 |
| 2011/0157593 | A1* | 6/2011 | Miyadera | G01N 21/553 356/445 |
| 2014/0315760 | A1* | 10/2014 | Ratner | G01N 33/54373 506/18 |
| 2016/0282265 | A1* | 9/2016 | Su | G01N 21/7746 |
| 2018/0120278 | A1* | 5/2018 | Hoorfar | G01N 33/497 |

OTHER PUBLICATIONS

Lee, et al., "Design and Implementation of Gas Sensor Array Based on Fluorescence Quenching Detection Using CMOS-MEMS Process," 2017 19th International Conference on Solid-State Sensors, Actuators and Microsystems (Transducers), IEEE, Jun. 18, 2017, pp. 672-675.

Lang, et al., "Nanomechanics from Atomic Resolution to Molecular Recognition Based on Atomic Force Microscopy Technology," Nanotechnology, vol. 13, 2002, pp. R29-R36.

International Search Report issued in PCT/FR2018/052219, dated Jan. 3, 2019, pp. 1-3.

* cited by examiner

DETECTION SYSTEM FOR AN ELECTRONIC NOSE AND AN ELECTRONIC NOSE COMPRISING SUCH A SYSTEM

CROSS-REFERENCE TO RELATED APPLICATIONS

This application is a 371 National Stage Entry of PCT Application No. PCT/FR2018/052219, filed Sep. 11, 2018, which claims priority to FR Application No. 1758547, filed Sep. 14, 2017, the disclosure of which is hereby incorporated by reference in its entirety.

TECHNICAL FIELD

The invention is in the field of electronic noses.

More specifically, the invention relates to an improved detection system for an electronic nose as well as an electronic nose comprising such a detection system.

The invention has many applications and, in particular, in the protection of the environment, in particular for the monitoring of olfactory pollution and the quality of more or less confined environments, in the monitoring of sites manufacturing, storing, handling and/or likely to be contaminated by potentially dangerous or odorous volatile materials, in health, for example to provide a substitute for the sense of smell to persons suffering from anosmia or to detect volatile biological markers, in the food industry, for example for the detection of contamination in a food manufacturing and/or distribution chain, as well as for the inspection of any product with an odor.

BACKGROUND

An "electronic nose" is a device for detecting and identifying odors and, therefore, target compounds in the gas phase.

The electronic nose owes its name to the analogy between its operation and that of the human olfactory system.

An electronic nose consists of three main systems, namely:

(1) a sampling system for the gas phase to be analyzed;

(2) a detection system which comprises a network of sensors capable of interacting in a physicochemical manner with the target compounds, the sensors playing the role of olfactory receptors;

(3) a computer system for processing and analyzing the responses emitted in the form of signals by the sensors in the form of signals as a result of a physicochemical interaction, this system playing the role of the brain.

By way of example of an electronic nose, mention may be made of the one presented by S. Brenet et al. at the 17th International Symposium on Olfaction and Electronic Noses (May 28-31, 2017, Montreal, Canada) and described in 2017 *ISOCS/IEEE International Symposium on Olfaction and Electronic Nose (ISOEN)*, IEEE, 2017, pp. 1-3, hereafter reference [1]. This electronic nose is designed to detect and identify volatile organic compounds and includes an optical detection system using surface plasmon resonance imaging (SPRi).

Like all analytical devices whose operation is based on the emission of signals from sensors, electronic noses are the seat, on the one hand, of parasitic signals that are grouped together under the name of "measurement noise", which are superimposed on the useful signals, i.e. the information that is sought to be recovered, and, on the other hand, on sensor drift.

Measurement noise can be caused by a multitude of factors external or internal to the electronic nose, such as variations in temperature, pressure, humidity and, in particular, by fluctuations in the measuring system due to variations in the aforementioned factors during measurement. This noise can occur at any time and lead to errors in the interpretation of the signals emitted by the sensors.

Sensor drift consists of a gradual long-term variation in the signals emitted by the sensors which is observed when the sensors are exposed to the same target compounds under the same operating conditions. It is induced by complex physicochemical mechanisms: it could be due in particular to poisoning of the sensors or their aging, but it could also be due to changes in physical, environmental parameters (such as temperature, pressure and humidity) and/or experimental parameters (such as a phenomenon of heating of the components of the electronic nose).

In biosensors or biochips, whose operation is based on the lock-and-key principle, i.e. a biologically active molecule (for example an antigen) is recognized by a specific ligand (for example an antibody specific to that antigen), ligands that are not specific to the molecules to be analyzed are generally used as negative controls in order to determine the measurement noise and any sensor drift and thus validate the signals emitted by these sensors.

Similarly, in chemical gas multisensors whose operation is based on an interaction between gases and gas-specific sensors, it is known to provide for the presence of a reference sensor to compensate for measurement noise, this sensor being typically an area of the multisensor which is free of sensitive material as described, for example, by Y. C. Lee et al. (19th *International Conference on Solid-State Sensors, Actuators and Microsystems (Transducers)*, IEEE, 2017, pp. 672-675, hereinafter reference [2]) for measuring a fluorescence reference (insensitive to the chemical environment). In this case, the gaseous compounds will quench the fluorescence signal of the sensors.

On the other hand, in electronic noses, whose operation is based on the principle of cross-reactivity, i.e. each ligand, called a receptor, interacts with more or less affinity with the target compounds, all the signals emitted by the sensors are taken into account, whether they are strong or weak, and it is all of these signals that constitute a recognition pattern, this pattern being characteristic of a target compound and can be considered as a digital fingerprint of this compound (see reference [1]).

Thus, in the case of electronic noses, it is currently impossible to determine whether the weakness of a signal emitted by a sensor corresponds to a lack of affinity of this sensor for one or more target compounds or to measurement noise.

To determine potential sensor drift, it has been proposed to use one or more reference gases (see *Handbook of Machine Olfaction: Electronic Nose Technology*, chapter 13, John Wiley & Sons 2006, hereafter reference [3]). The idea is to carry out measurements with the reference gas(es) at the beginning of the measurement series and then at certain time intervals for as long as the sensors are used. The change in response of the sensors to the reference gas(es) is taken as a measure of the change in response for all other measurements. Therefore, in order to obtain a good estimate of the drift for gas samples to be analyzed, a reference gas should be found that perfectly reflects the drift that can be obtained with these samples. It is very difficult however, if not impossible, to find such a reference gas.

In addition, many methods have been developed to reduce the effects of drift. They are often based on mathematical models to compensate for changes in sensor performance.

These methods can be divided into four main categories: those involving pre-processing of sensor signals, periodic calibration, data harmonization methods and adaptive methods (see S. Di Carlo and M. Falasconi, *Drift correction methods for gas chemical sensors in artificial olfaction systems: techniques and challenges.* InTech: 2012, hereinafter reference [4]). If some of these methods such as adaptive methods (neural networks, evolutionary algorithms, etc.) seem promising, they are still difficult to use in practice.

As a result of the above, the determination of measurement noise and/or sensor drift of an electronic nose unit and, if drift occurs, the reduction of the effects of this drift remains a major problem, as the existence of high noise and/or sensor drift may hamper the use of this type of instrument, as well as the lack of reliability and reproducibility.

The invention aims precisely at providing a solution to this problem.

SUMMARY OF THE INVENTION

Therefore, first, the invention relates to a detection system for an electronic nose capable of detecting and identifying a set S of compounds likely to be present in a gaseous sample, which detection system comprises a plurality of cross-reactive detection sensors for providing signals representative of the presence of one or more compounds of the set S in the gaseous sample, each detection sensor comprising a sensitive part, and is characterized in that it comprises:

at least one reference sensor for providing a signal representative of the measurement noise of the detection system, the reference sensor comprising a sensitive part;

a substrate comprising a surface on which the sensitive parts of the detection sensors and the sensitive part of the reference sensor are arranged; and in that the surface of the substrate comprises:

a plurality of sensitive areas, each of said sensitive areas corresponding to the sensitive portion of one of the detection sensors and comprising at least one receptor capable of interacting physicochemically with at least one compound of the set S; and at least one sensitive area which corresponds to the sensitive part of the reference sensor and which is functionalized with at least one fluorinated compound chosen from compounds comprising at least one perfluorinated terminal alkyl group and fluorinated polymers.

Thus, according to the invention, it is proposed to provide, in a detection system for an electronic nose, for the presence of at least one sensor (i.e. one or more sensors) whose function is not to provide information on the compounds likely to be present in the gaseous sample but to provide information on the measurement noise of this detection system and, consequently, to allow correction of any possible drifts of the measurement noise and/or of the detection sensors.

It is further proposed that the sensitive part of the reference sensor(s) be functionalized with at least one fluorinated compound, this compound being selected from compounds comprising at least one perfluorinated terminal alkyl group, i.e. at least one —$CF_3$ group, and fluorinated polymers, this type of compounds and polymers having the advantage of having both chemical inertness and non-wetting properties.

In the foregoing and the following:

"sensor" means an assembly which comprises a sensitive part which comprises at least one receptor capable of interacting in a physicochemical manner with at least one of the compounds of the set S, and a measuring system, typically called a transducer, whose function is to measure a variation in a physical quantity resulting from the physicochemical interaction and to convert this measurement into a usable signal, it being understood that each of the sensors of the detection system may comprise its own measuring system or share with other sensors a measuring system common to them;

"cross-reactivity" means that the sensitive part of a detection sensor can interact in a physicochemical manner with different compounds of the set S and that, conversely, a compound of the set S can interact in a physicochemical manner with the sensitive part of different detection sensors;

"measurement noise" means that part of a signal emitted by a sensor which is induced by factors other than its physicochemical interaction with one of the compounds of the set S, for example a variation in temperature, a variation in pressure, a variation in humidity, a variation in the electrical supply voltage of the detection system, vibrations, etc.;

"measuring system drift" means a gradual change over time in the average level of measurement noise; and "sensor drift" means a progressive variation over time of the signal emitted by a sensor with respect to the signal that this sensor is supposed to emit under the same conditions, i.e. when it is exposed to the same gas sample and with the same operating parameters; the drift of a sensor corresponds to the sum of the drift of the measuring system and the chemical drift of the sensor, i.e. a progressive variation over time of the capacity of the sensitive part of this sensor to interact in a physicochemical manner with at least one of the compounds of the set S.

In addition, "receptor" means any chemical molecule, simple or complex (i.e. being able, in particular, to be a macromolecule), which, by itself or when it is associated with one or more other receptors within a mixture of receptors, is capable of interacting in a physicochemical manner with one or more compounds of the set S, this physicochemical interaction typically residing in sorption and, more specifically, adsorption.

Preferably, the fluorinated compound is selected from compounds of formula $C_vF_{2v+2}$ in which v is an integer ranging from 4 to 20, and compounds of formula $C_wF_{2w+1}$-$(L)_x$-Z in which w is an integer ranging from 1 to 12, x is 0 or 1, L represents a divalent spacer group while Z represents a group capable of allowing the attachment, by covalent or non-covalent bonds, of the compound on the surface of the substrate.

The divalent spacer group may in particular be a linear or branched, saturated or unsaturated hydrocarbon group comprising from 1 to 20 carbon atoms and optionally one or more heteroatoms, this heteroatom or these heteroatoms being typically chosen from oxygen, nitrogen, sulfur and silicon. Thus, the divalent spacer group is, for example, a divalent alkylene group comprising from 1 to 20 carbon atoms and, more preferably, from 1 to 12 carbon atoms.

Advantageously, Z represents a thiol, amino, silanol, carbonyl or carboxyl group.

According to a particularly preferred embodiment of the invention, the fluorinated compound is a perfluoroalkanethiol of formula $CF_3(CF_2)_y(CH_2)_zSH$ in which y is an integer from 0 to 11 and z is an integer from 1 to 20 and preferably from 1 to 12.

By way of examples of such a fluorinated compound, mention may be made of 1H,1H-trifluoroethanethiol, 1H,1H,2H,2H-perfluoropentanethiol, 1H,1H,2H,2H-perfluorohexanethiol, 1H,1H,2H,2H-perfluorooctanethiol and 1H,1H,2H,2H-perfluorodecanethiol.

As mentioned above, the fluorinated compound may also be a fluoropolymer, in which case it is advantageously selected from polytetrafluoroethylenes, polyvinyl fluorides, polyvinylidene fluorides, perfluoroalkoxy alkanes, fluorinated ethylene-propylene copolymers and poly(ethylene-co-tetrafluoroethylene).

In accordance with the invention, the sensitive area corresponding to the sensitive part of the reference sensor can be formed by any of the surface functionalization techniques known to the skilled person such as physical or chemical adsorption, covalent grafting, molecular jet epitaxy, thin film deposition, molecular self-assembly, etc., it being understood that the choice of this technique will depend on the chemical nature of the surface of the substrate, the chemical nature and molecular size of the compound used to functionalize said sensitive area and the measuring system of the reference sensor.

Among these techniques, preference is given, in the context of the invention, to molecular self-assembly.

According to another particularly preferred embodiment of the invention, the surface of the substrate is a passivated surface, i.e. it has been subjected to a treatment suitable for minimizing the physicochemical interactions that may occur between this surface and the compounds of the set S and, consequently, for reducing the poisoning and aging of the sensitive parts of the detection sensors.

In which case, the surface of the substrate is preferably passivated with at least one fluorinated compound which is also selected from compounds comprising at least one perfluorinated terminal alkyl group and fluorinated polymers and, in particular, those previously mentioned.

In accordance with the invention, this fluorinated compound may be the same compound with which the sensitive area corresponding to the sensitive part of the reference sensor is functionalized or may be a different compound, provided that it is selected from compounds comprising at least one perfluorinated terminal alkyl group and fluorinated polymers.

As previously indicated, each of the sensors included in the detection system may comprise its own measuring system—or transducer—or share with other sensors a measuring system common to them. In both cases, the measuring system can be any measuring system that generates a usable signal during the physicochemical interaction between a compound in the gaseous state and the sensitive part of a sensor and can, in particular, be of the resistive, piezoelectric, mechanical, acoustic or optical type. In other words, the sensors can be resistive, piezoelectric, mechanical, acoustic and/or optical sensors.

However, for the purposes of the invention, it is preferred that the sensors be optical surface plasmon resonance sensors. This type of transduction, which is known per se, generally combines a light source, for example of the LED type, to cause plasmon excitation and a CCD camera to record the signal resulting from the plasmon resonance. As such, it is particularly preferable that the signals emitted by the sensors be tracked in imaging mode, which consists of following the signal variations of all the pixels making up the image of the CCD camera used.

The substrate is made of a material suitable for the measuring system. Thus, if the measurement is performed by surface plasmon resonance, then the substrate preferably comprises a glass prism, one side of which is coated with a metal layer, preferably gold or silver, typically 10 nm to 100 nm thick. This metal layer can be passivated as previously mentioned.

As will be shown in the following examples, the invention has many advantages.

In fact, by providing the detection system with a reference sensor whose function is to provide a signal representative of the measurement noise of this detection system, the invention makes it possible, in addition to knowing this measurement noise and, therefore, to subtract it from the signals emitted by the detection sensors, greater reliability and reproducibility of the operation of the electronic nose unit, to detect any drift of the measuring system as well as any drift of the detection sensors and, consequently, to correct the signals emitted by the detection sensors accordingly, again with greater reliability and reproducibility of the operation of the electronic nose unit.

In addition, by providing for passivating the surface of the substrate on which the sensitive parts of the detection sensors and the reference sensor of the detection system are or will be arranged, the invention furthermore reduces the drift of the detection sensors, the poisoning and the aging of the sensitive parts of the detection sensors and, thus, provides greater stability and longevity of the electronic nose.

The invention also relates to an electronic nose capable of detecting and identifying a set S of compounds likely to be present in a gaseous sample, which electronic nose is characterized in that it comprises a detection system as previously described.

In accordance with the invention, the electronic nose is preferably dedicated to the detection and identification of volatile organic compounds, hydrogen sulfide ($H_2S$) and ammonia ($NH_3$), it being possible for these compounds to be present alone or as a mixture in the gaseous sample.

In the foregoing and the following, a "volatile organic compound" is defined in accordance with European Council Directive 1999/13/EC of 11 Mar. 1999 which states that:

a volatile organic compound is "any organic compound having a vapor pressure of 0.01 kPa (i.e. $9.87 \cdot 10^{-5}$ atm) or more at a temperature of 293.15 K (i.e. 20° C.) or having a corresponding volatility under the particular conditions of use" (see paragraph 17 of Article 2 of the Directive);

an organic compound is "any compound comprising at least the carbon element and one or more of the following elements: hydrogen, halogens, oxygen, sulfur, phosphorus, silicon or nitrogen, with the exception of carbon oxides and inorganic carbonates and bicarbonates" (see paragraph 16 of Article 2 of the Directive).

Thus, the following are in particular considered to be volatile organic compounds: certain saturated or unsaturated acyclic hydrocarbons, such as ethane, propane, n-butane, n-hexane, ethylene, propylene, 1,3-butadiene and acetylene, certain saturated or unsaturated non-aromatic cyclic hydrocarbons, such as cyclopropane, cyclopentane and cyclohexane, certain aromatic hydrocarbons such as benzene, toluene, xylenes and ethylbenzene, certain halogenated hydrocarbons such as dichloromethane, trichloromethane, chloroethane, trichloroethylene and tetrachloroethylene, certain alcohols such as methanol, ethanol, 1-propanol, 2-propanol, ethylene glycol and propylene glycol, certain aldehydes such as formaldehyde, acetaldehyde, propanal and 2-propenal (or acrolein), certain ketones such as acetone, methyl ethyl ketone, 2-butanone and methyl vinyl ketone, certain esters such as methyl acetate, ethyl acetate, isopropyl acetate and isoamyl butyrate, certain ethers such as diethyl ether, ethylene glycol n-butyl ether (EGBE) and 1,4-dioxane, certain acids such as acetic acid and propanoic acid, certain amines such as ethylamine, dimethylamine, trimethylamine, diethylamine and amylamine, certain amides such as dimethylformamide, sulfur compounds such as methyl mercaptan (or methanethiol) and ethyl mercaptan (or ethanethiol), and certain nitriles such as acetonitrile and acrylonitrile.

Other features and advantages of the invention will be apparent from the following additional description, which is given with reference to the appended figures.

However, it goes without saying that this additional description is given only as an illustration of the subject matter of the invention and should in no way be interpreted as a limitation of that subject matter.

BRIEF DESCRIPTION OF THE FIGURES

In FIGS. 1 to 3, the same elements are designated by the same reference marks.

DETAILED DISCLOSURE OF PARTICULAR EMBODIMENTS

Figure 1:
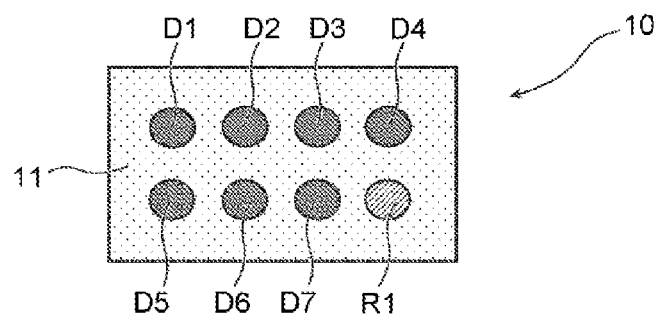
FIGS. 1 to 3 schematically illustrate three example embodiments of the substrate of a detection system according to the invention, in which the sensitive parts of the detection sensors and the reference sensors are arranged on the surface of a common substrate.

I—Example Embodiments of the Substrate of a Detection System According to the Invention Reference is made first to FIG. 1, which schematically illustrates a first embodiment of the substrate 10 of a detection system according to the invention, in which the sensitive parts of the detection sensors and the reference sensors are arranged on the surface of the same substrate.

As can be seen in this figure, the substrate 10 comprises a surface 11 on which is arranged a plurality of sensitive areas referenced D1, D2, D3, D4, D5, D6 and D7 respectively, each of which correspond to the sensitive part of a detection sensor and which will therefore be referred to as "detection sensitive areas" hereinbelow. There are 7 of these sensitive areas in FIG. 1 for the sake of simplification of this figure and thus correspond to 7 detection sensors.

However, it goes without saying that it is possible to design a detection system according to the invention comprising a much larger number of detection sensors, for example 100, 500, 1000, 3000 or even 5000 detection sensors, and thus a substrate on the surface of which a corresponding number of detection-sensitive areas are arranged.

The surface 11 of the substrate 10 also includes a sensitive area referenced R1, which corresponds to the sensitive part of a reference sensor and will therefore be referred to as a "reference sensitive area" hereinbelow. Again, for the sake of simplicity, FIG. 1 shows only one reference sensitive area, corresponding to one reference sensor.

However, here too, it is possible to design a detection system comprising a plurality of reference sensors, for example 5, 10 or even 50 reference sensors and, thus, a substrate on the surface of which a corresponding number of reference sensitive areas are arranged.

In accordance with the invention, the detection sensitive areas D1 to D7 can be created by functionalizing seven distinct areas of the surface 11 of the substrate 10 with one or more receptors, i.e. of one or more compounds capable of interacting in a physicochemical manner, typically by adsorption and, more specifically, adsorption mechanism, with at least one of the compounds of the set S of compounds which the electronic nose is capable of detecting and identifying in a gaseous sample.

This functionalization can be achieved by means of any of the surface functionalization techniques known to the skilled person (physical or chemical adsorption, covalent grafting, molecular jet epitaxy, thin film deposition, molecular self-assembly, etc.) or by several of these, the choice of this technique or these techniques being in particular a function of the chemical nature of the surface of the substrate, the chemical nature and molecular size of the receptors and the measurement system of the detection sensors.

In the case where the compounds of the set S are VOCs, $H_2S$ and $NH_3$, then the receptors can be chosen notably among metals, metal oxides, non-fluorinated organic compounds, non-fluorinated polymers, biomolecules such as DNA molecules, oligonucleotides, sugars, peptides, proteins, phospholipids, and derivatives of these biomolecules, or among the different molecular arrangements of carbon such as graphene, nanotubes, graphite carbon, etc. In this regard, the reader may refer to the articles by K. Arshak et al. in *Sensor Review* 2004, vol. 24, pp. 181-198; T. Wasilewski et al., *Biosensors and Bioelectronics* 2017, vol. 87, pp. 480-494; and A. D. Wilson and M. Baietto, *Sensors* (Basel) 2009, vol. 9, pp. 5099-5148, hereafter references [5] to [7], for more ample information on the types of receptors that could be used.

The reference sensitive area R1 can be created by functionalizing an area on the surface 11 of the substrate 10, which is distinct from the detection sensitive areas D1 to D7, with one or more compounds that do not interact physico-chemically with compounds of the set S or, if they interact with one or more of these compounds, give rise to very weak interactions compared to those that are likely to occur between the receptors of the sensitive areas D1 to D7 and said compounds of the set S.

Here again, this functionalization can be achieved by means of any of the surface functionalization techniques known to the skilled person as a function of the chemical nature of the substrate, the chemical nature and molecular size of the compound(s) and the measuring system of the reference sensor.

In accordance with the invention, the compound or compounds which do not interact or interact only very weakly with the compounds of the set S are selected from fluorinated compounds comprising at least one perfluorinated terminal alkyl group, i.e. at least one —$CF_3$ group, and fluorinated polymers due, on the one hand, to the chemical inertness which characterizes these type of compounds and polymers and, on the other hand, to their non-wetting properties.

Fluorinated compounds having at least one perfluorinated terminal alkyl group may in particular be perfluorinated compounds, i.e. compounds of formula $C_vF_{2v+2}$ in which v is an integer from 4 to 20, or compounds of formula $C_wF_{2w+1}$-$(L)_x$-Z in which w is an integer from 1 to 12, x is 0 or 1 and L is a divalent spacer group, for example a linear or branched, saturated or unsaturated hydrocarbon group comprising from 1 to 20 carbon atoms and optionally one or more heteroatoms, typically O, N, S and/or Si, while Z represents a group capable of allowing the compounds to be attached, by covalent or non-covalent bonds, to the surface of the substrate.

For functionalization by molecular self-assembly—which is the functionalization technique which is preferred in the context of the invention—the group Z may, for example, be a thiol (—SH) or amino (—NH$_2$) group if the surface of the substrate is of gold, platinum, silver, palladium or copper, or else a silanol (—SiOH) group if the surface of the substrate is of glass, quartz, silicon or silica.

Among the compounds of formula $C_wF_{2w+1}$-$(L)_x$-Z, preference is given to perfluoroalkanethiols of formula $CF_3(CF_2)_y(CH_2)_zSH$ in which y is an integer ranging from 0 to 11 and z is an integer ranging from 1 to 20 and, better still, from 1 to 12, such as the 1H,1H-trifluoroethanethiol of formula $CF_3CH_2SH$, the 1H,1H,2H,2H-perfluoropentanethiol of formula $CF_3(CF_2)_2(CH_2)_2SH$, the 1H,1H,2H,2H-perfluorohexanethiol of formula $CF_3(CF_2)_3(CH_2)_2SH$, the 1H,1H,2H,2H-perfluorooctanethiol of formula $CF_3(CF_2)_5(CH_2)_2SH$ and 1H,1H,2H,2H-perfluorodecanethiol of formula $CF_3(CF_2)_7(CH_2)_2SH$, all available from SIGMA-ALDRICH.

Fluorinated polymers likely to be used include in particular polytetrafluoroethylenes (PTFE) such as those marketed by DUPONT under the name Teflon™, polyvinyl fluorides (PVF) such as those marketed by DUPONT under the name Tedlar™, and polyvinylidene fluorides (PVDF) such as those marketed by ARKEMA under the name Kynar™, perfluoroalkoxy alkanes (PFA) such as those marketed by DUPONT under the name Teflon™-PFA, fluorinated ethylene-propylene copolymers (also known as fluorinated ethylene-propylenes or FEP) such as those marketed by DUPONT under the name Teflon™-FEP, and poly(ethylene-co-tetrafluoroethylenes) (ETFE) such as those marketed by DUPONT under the name Tefzel™.

Figure 2:
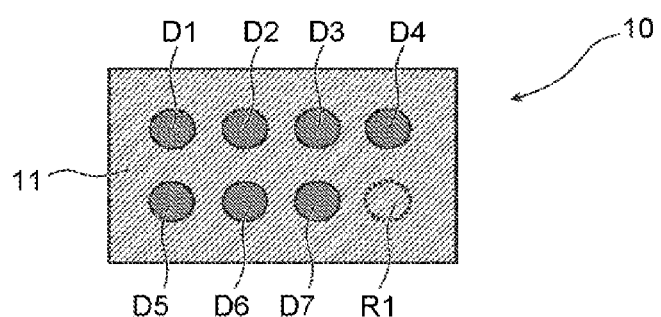

Reference is now made to FIG. 2, which schematically illustrates a second embodiment of the substrate 10 of a detection system according to the invention, in which the sensitive parts of the detection and reference sensors are also arranged on a common substrate.

In this example, the substrate 10 differs from that shown in FIG. 1 only in that its surface 11 has been subjected to a passivation treatment with the same compound or compounds as that or those forming the reference sensitive area R1.

In the case where the detection sensitive areas D1 to D7 are created by covalent grafting or by molecular self-assembly and where the passivation treatment is itself carried out by means of one of these two techniques, then this passivation treatment can be carried out after the creation of the detection sensitive areas D1 to D7, in which case only those parts of the surface 11 of the substrate 10 left free by the detection sensitive areas D1 to D7 are passivated and the reference sensitive area R1 is selected on one of these passivated parts.

Alternatively, the passivation treatment can also be carried out before the creation of the detection sensitive areas D1 to D7, in which case these sensitive areas can be created either by covering, at seven distinct areas of the surface 11 of the substrate 10, the passivation compound or compounds present on these areas with one or more receptors or by depassivating seven distinct areas of the surface 11 of the substrate 10, for example by lithography, and by functionalizing the areas thus depassivated with one or more receptors. Here too, the reference sensitive area R1 can then be chosen on one of the parts of the surface 11 of the substrate 10 left free by the detection sensitive areas D1 to D7.

Figure 3:
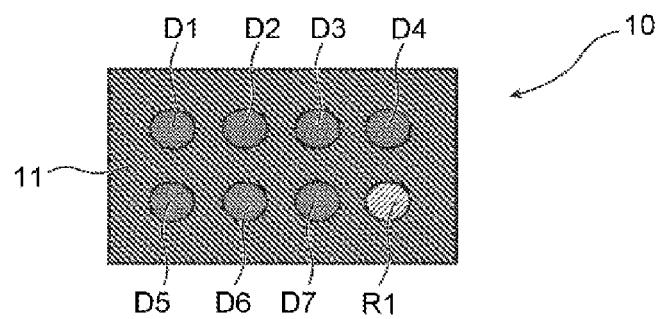

FIG. 3 schematically illustrates a variant of the second example embodiment of the substrate 10 of a detection system according to the invention, in which variant the surface 11 of the substrate 10 has been subjected to a passivation treatment with one or more compounds which are different from that or those forming the reference sensitive area R1 but which are also selected from compounds comprising a perfluorinated terminal alkyl group and fluorinated polymers.

Thus, for example, it is possible to use two different compounds selected from perfluorinated compounds and compounds of formula $C_wF_{2w+1}$-$(L)_x$-Z as previously defined to form the reference sensitive area R1 and passivate the surface 11 of the substrate.

Alternatively, it is also possible to use a perfluorinated compound or a compound of formula $C_wF_{2w+1}$-$(L)_x$-Z as previously defined to form the reference sensitive area R1 and to passivate the surface 11 of the substrate 10 with a fluorinated polymer such as PTFE.

Here again, the passivation treatment can be carried out after or before the creation of the detection sensitive areas D1 to D7 and the reference sensitive area R1 in the same ways as described above.

It should be noted that since FIGS. 1 to 3 correspond to schematic illustrations of embodiments of the detection system according to the invention, the sensitive areas D1 to D7 and R1 are represented in a circular form on these figures.

However, it goes without saying that the detection sensitive areas and the reference sensitive areas may have a completely different shape, for example polygonal and, in particular, parallelepipedal, or be of any shape.

Similarly, the sensitive areas D1 to D7 and R1 are shown separately from each other in FIGS. 1 to 3, but it is quite conceivable that the detection sensitive areas and the reference sensitive areas are adjacent to each other.

II—Properties of a Detection System According to the Invention with a Non-Passivated Substrate II.1—Demonstration by Imagery of the Difference in Sensitivity Existing Between the Detection Sensors and the Reference Sensors with Respect to VOCs:

The present test was carried out using a substrate consisting of a glass prism, covered on one of its faces with a layer of chromium (about 2 nm thick), itself covered with a layer of gold (about 50 nm thick) and comprising:

a plurality of detection sensitive areas, these areas being formed of self-assembled layers of different cross-reactive receptors (i.e. a receptor can interact with different VOCs and, conversely, a VOC can react with different receptors), each of the receptors comprising a thiol function for its attachment to the gold layer, and a plurality of reference sensitive areas, these areas being formed of self-assembled layers of 1H,1H,2H,2H-perfluorodecanethiol, this self-assembly having been carried out by microdeposition, by means of a robot, of a solution comprising 7 mmol/L of this compound on the gold layer.

This substrate was exposed for 10 minutes to a gaseous sample comprising a VOC, in this case isoamyl butyrate $(CH_3(CH_2)_2C(O)O(CH_2)_2CH(CH_3)_2)$ at a concentration of about 30 ppm, and the interactions between this VOC and the various sensitive areas of the substrate were monitored by surface plasmon resonance imaging (SPRi).

Figure 4:
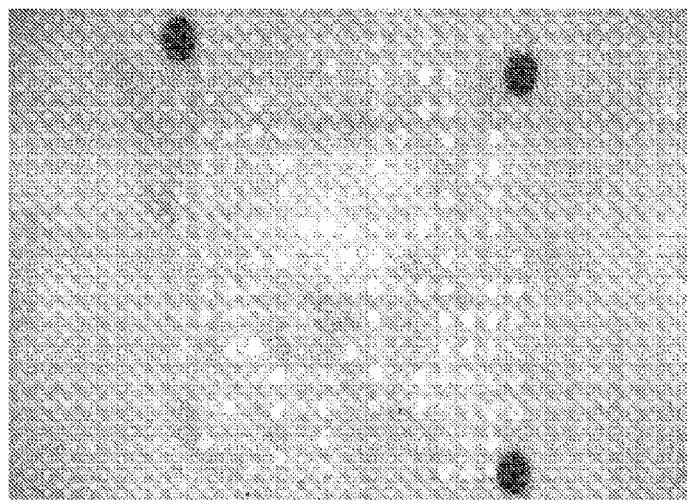
FIG. 4 is a differential image obtained by surface plasmon resonance imaging (SPRi) after exposure of a detection system according to the invention, with a non-passivated substrate, to a gaseous sample comprising a VOC, in this case isoamyl butyrate.

The differential image shown in FIG. 4 was thus obtained.

SPRi is a technique for optically reading surface interactions that can be likened to an optical balance: the more interactions there are between a compound and a surface, the more the optical signal emitted by the reading system increases. A differential image represents the variation of this optical signal with respect to a reference image taken before the surface was exposed to the compound. Also, the brighter an area of the differential image, the greater the physicochemical interaction between the compound and the corresponding area of the surface. Conversely, the darker an area of the differential image, the lower the physicochemical interaction between the compound and the surface area.

As shown in the figure, the differential image has areas that are very bright or even white, corresponding to the detection sensitive areas of the substrate to which isoamyl butyrate has adsorbed, and areas that are black, corresponding to the reference sensitive areas of the substrate to which isoamyl butyrate has not adsorbed or has adsorbed very little, which demonstrates that areas of a substrate which are functionalized by 1H,1H,2H,2H-perfluorodecanethiol have true chemical inertness towards VOCs such as isoamyl butyrate.

11.2—Comparison Between the Sensitivity with Respect to VOCs of Sensors Whose Sensitive Parts are Formed of a Perfluoroalkanethiol and that of Sensors Whose Sensitive Parts are Formed of a Non-Fluorinated Alkanethiol:

The present test was carried out using a series of substrates consisting of glass prisms, coated on one of their faces with a layer of gold (approximately 50 nm thick) and comprising, on the one hand, areas formed of self-assembled layers of 1H,1H,2H,2H-perfluorodecanethiol and, on the other hand, areas formed of self-assembled layers of dodecanethiol ($CH_3(CH_2)_{11}SH$), the self-assemblies having been obtained by microdeposition, by means of a robot, of solutions comprising from 5 mmol/L to 10 mmol/L of one of these compounds on the gold layer.

These substrates were exposed to gaseous samples comprising 20 ppm isoamyl butyrate and the interactions between this VOC and the different self-assembled layers present on the substrates were monitored by SPRi.

Figure 5:
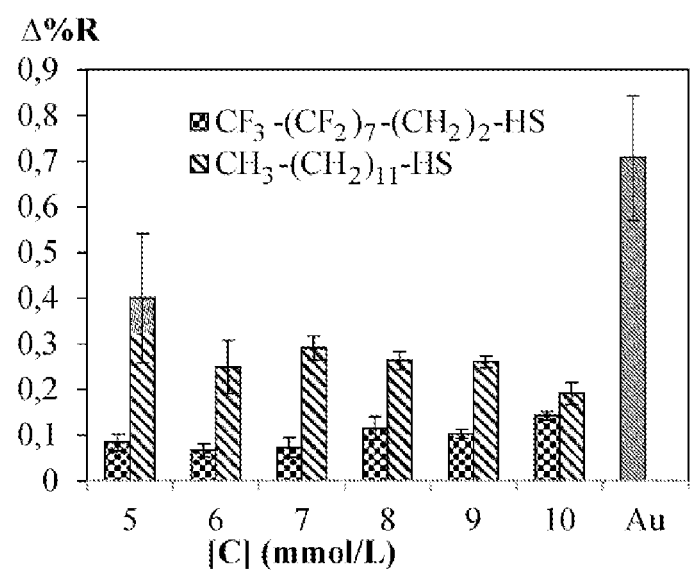
FIG. 5 shows, in the form of a bar graph, the variation in reflectivity, denoted $\Delta\% R$, as obtained by SPRi for self-assembled layers of 1H,1H,2H,2H-perfluorodecanethiol and dodecanethiol arranged on the surface of a substrate, as a function of the concentration, denoted [C] and expressed in mmol/L, of the solutions from which these self-assembled layers were obtained; is also represented the variation in reflectivity obtained for an area of the gold layer (bar denoted Au) forming the surface of the substrate.

The results of this test are shown in FIG. 5 which shows, in the form of a bar graph, the variation in reflectivity, denoted as Δ% R, as obtained for each of the two types of layers and for each of the concentrations, denoted [C] and expressed in mmol/L, of the solutions from which these layers were obtained. By way of comparison, FIG. 5 also shows the variation in reflectivity obtained for an area of the gold layer (bar denoted Au).

As shown in this figure, the variation in reflectivity observed for the self-assembled dodecanethiol layers—which reflects the sensitivity of these layers to isoamyl butyrate—although lower than that observed for the gold layer, is systematically higher than that observed for the 1H,1H,2H,2H-perfluorodecanethiol layers, regardless of the concentration of the solution used to deposit these layers.

Consequently, the adsorption of isoamyl butyrate on the dodecanethiol layers is systematically higher than that on the 1H,1H,2H,2H-perfluorodecanethiol layers.

As also shown in this figure, the variation in the reflectivity of the self-assembled layers depends on the concentration of the solution used for the deposition of these layers. In the case of 1H,1H,2H,2H-perfluorodecanethiol, the lowest variation in reflectivity is observed for a concentration ranging from 6 mmol/L to 7 mmol/L, a concentration at which this variation is more than twice as low as that obtained for the self-assembled layers of dodecanethiol.

11.3—Verification of the Functionality of the Reference Sensors:

To ensure that the dark areas observed in the image in FIG. 4 are indeed due to an absence or quasi absence of physicochemical interaction between isoamyl butyrate and the reference sensitive areas of the substrate described in Example 11.1 above, this substrate was exposed to a gaseous sample consisting solely of air (and, therefore, free of any chemical compound likely to interact with detection sensitive areas) and the plasmon curves were established by SPRi for the detection and reference sensitive areas.

Figure 6:
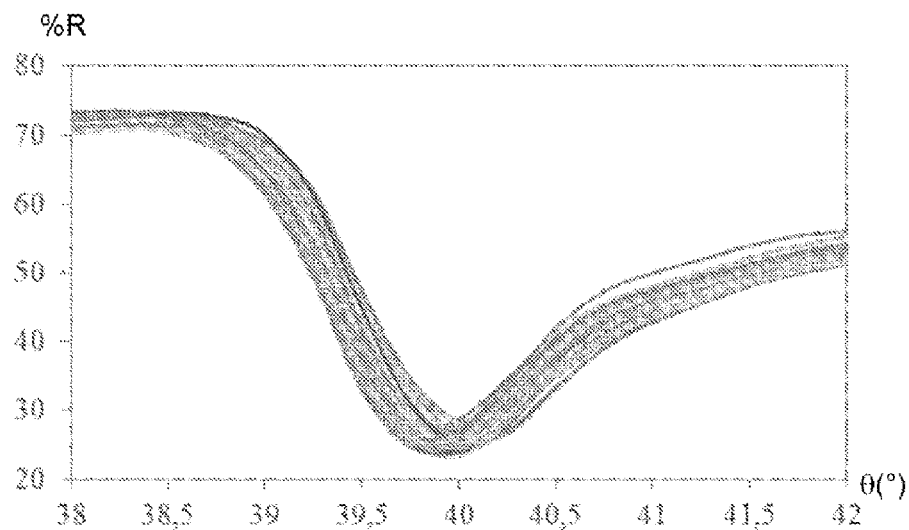
FIG. 6 shows the curves of the plasmons as obtained by SPRi for the detection sensors and reference sensors of a detection system according to the invention, with a non-passivated substrate, after exposure to a gaseous sample consisting solely of air; in this figure, the y-axis corresponds to the reflectivity, denoted % R, while the x-axis corresponds to the angle of incidence, denoted $\Theta$ and expressed in degrees.

These curves are shown in FIG. 6.

As shown in this figure, the plasmon curves obtained for the reference sensitive areas are consistent with those obtained for the detection sensitive areas.

The dark areas observed in the image in FIG. 4 are therefore due to an absence or near absence of physicochemical interaction between isoamyl butyrate and the reference sensitive areas of the substrate and not to the fact that the SPRi would be outside its sensitivity range.

11.4—Sensitivity of Reference Sensors to Variations in Physical Parameters:

In order to verify that the reference sensitive areas of the substrate described in Example 11.1 above, although insensitive or only slightly sensitive to the presence of VOCs, are nevertheless sensitive to variations in environmental or experimental physical parameters, a test known as the "index jump" test was carried out.

The principle of this test is to vary the refractive index of a gaseous sample consisting solely of air (and therefore free of any chemical compound likely to interact chemically with the detection sensitive areas of the substrate) by means of a physical parameter and to observe whether or not the variation in the refractive index results in a variation in the optical signals obtained by SPRi for the detection sensitive areas and the reference sensitive areas of the substrate.

In this case, the test was performed by applying an overpressure (ΔP=0.5 bar) to the substrate.

Figure 7:
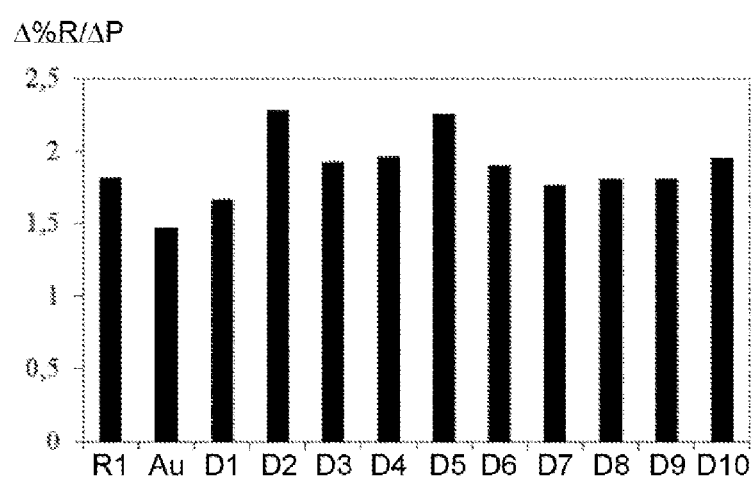
FIG. 7 illustrates, in the form of a bar graph, the ratio $\Delta\% R/\Delta P$ (variation of reflectivity to variation of pressure) as obtained by SPRi for ten detection sensors, denoted D1 to D10, and a reference sensor, denoted R1, of a detection system according to the invention, with a non-passivated substrate, in response to an overpressure ($\Delta P$); also represented is the ratio $\Delta A \% R/\Delta P$ obtained for an area of the gold layer, denoted Au, forming the surface of the substrate.

The results of this test are presented in FIG. 7, in the form of a bar graph expressing the ratio Δ% R/ΔP obtained for a reference sensitive area, denoted R1, ten detection sensitive areas, denoted D1 to D10, and for an area of the gold layer, denoted Au, of the substrate.

As shown in this figure, a variation in the refractive index of the gaseous sample having as its sole origin a variation in a physical parameter has resulted in an Δ% R/ΔP ratio which is comparable for all the sensitive areas of the substrate.

The sensitivity to variations in physical parameters can therefore be considered to be the same for all sensitive areas of the substrate.

The reference sensitive areas are therefore not or only slightly sensitive to VOCs while being sensitive to variations in physical parameters, in this case a variation in pressure. They can therefore be used as negative or zero references for the physicochemical interactions likely to occur on the substrate with VOCs.

11.5—Evaluation of Measurement Noise:

Insofar as, as shown in the preceding example, the reference sensitive areas of the substrate described in Example 11.1 above are sensitive to variations in physical parameters, the measurement noise of a detection system comprising such a substrate can be estimated by measuring the short-term fluctuation of the optical signals obtained for these sensitive areas when exposed to a gaseous sample comprising a VOC such as isoamyl butyrate.

Figure 8A:
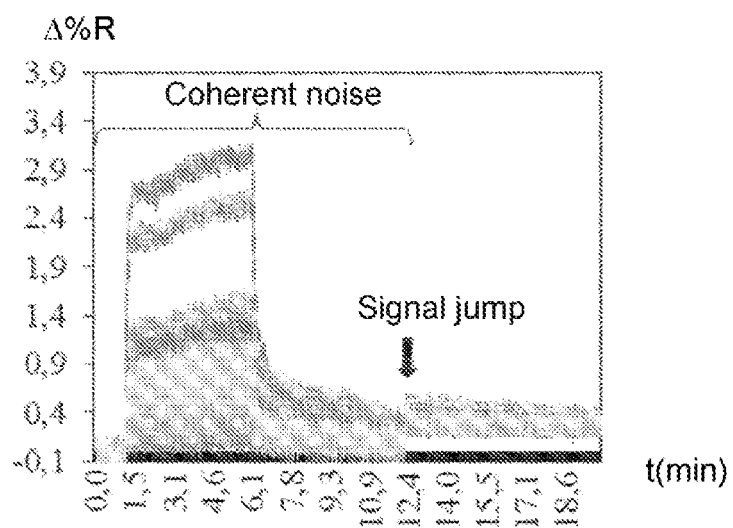
FIG. 8A shows the uncorrected variation in reflectivity, denoted $\Delta\% R$, as a function of time, denoted t and expressed in minutes, as obtained by SPRi for exposure to a gaseous sample comprising isoamyl butyrate, on which coherent noise and signal jump due to disturbances in the measuring system are observed, while FIG. 8B corresponds to FIG. 8A but after correction of the data by the reference sensor.

FIG. 8A shows that the measurement noise normally measured is approximately ±0.05% R (cf. from 14 to 18 minutes).

This figure also shows coherent noise, i.e. noise which is reflected in the same way on all optical signals emitted by the sensors (cf. from 0 to 12 minutes), as well as a signal jump. These phenomena are due to external parameters, for example vibrations in the case of coherent noise or a sudden change in pressure in the case of the signal jump. Since they are not related to chemical detection, they can be eliminated by means of the reference sensors of a detection system according to the invention, by subtracting the average optical signal obtained at a time t for the reference sensitive areas from that obtained at the same time t for each of the detection sensitive areas.

Figure 8B:
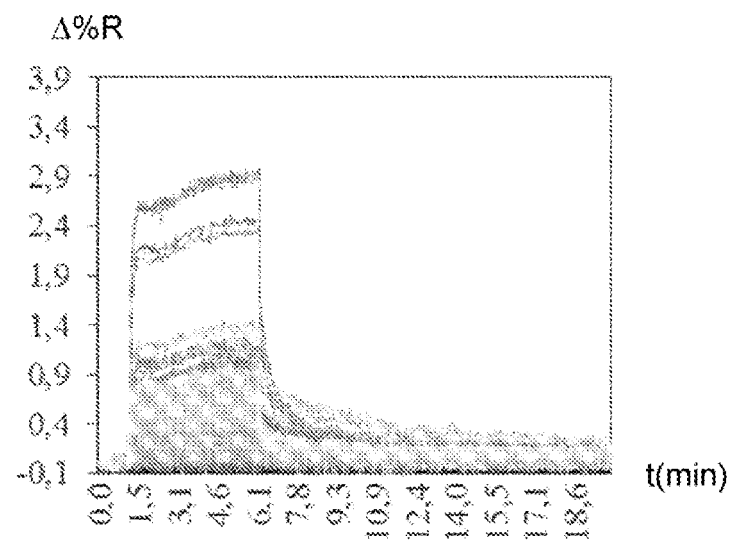

A "cleaned" optical signal, as shown in FIG. 8B, is thus obtained for each detection sensitive area.

11.6—Evaluation of the Measuring System Drift and the Drift of Each Detection Sensor:

A test consisting of exposing the substrate described in Example 11.1 above successively to five gaseous samples comprising, for the first 22 ppm isoamyl butyrate, for the second 3.2 ppm amylamine, for the third 4.2 ppm amylamine, for the fourth 5 ppm amylamine and for the fifth 14.20 ppm amylamine, over a total duration of 155 minutes and to monitor by SPRi the change in reflectivity for a reference sensitive area, denoted R1, and for two detection sensitive areas of this substrate, denoted D1 and D2, throughout the entire duration of this exposure.

Figure 9:
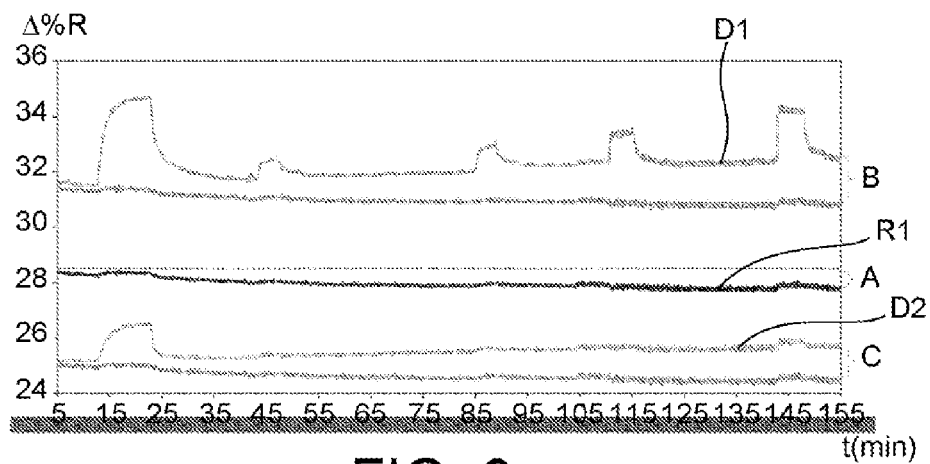
FIG. 9 illustrates the change in reflectivity, denoted % R, as a function of time, denoted t and expressed in minutes, as obtained by SPRi for two detection sensors (lines D1 and D2) and a reference sensor (line R1) of a detection system according to the invention, with a non-passivated substrate, over a period of 155 minutes during which these sensors were successively exposed to five gaseous samples comprising, for the first, isoamyl butyrate and, for the other four, amylamine; in this figure, bracket A symbolizes the drift of the measuring system; the line R1 has been duplicated below the lines D1 and D2 and the brackets B and C symbolize the chemical drift of the sensors D1 and D2 respectively.

FIG. 9 was thus established in which the line denoted R1 corresponds to the change in reflectivity, denoted % R, as observed for the area R1, while the lines denoted D1 and D2 represent the change in % R as observed for the areas D1 and D2 respectively. In this figure, the line R1, which corresponds to the drift of the measuring system, has been duplicated below each of the lines D1 and D2.

As previously mentioned, the measuring system drift is a progressive variation over time of the average level of the measurement noise, or signal baseline, which can be caused by complex phenomena, which may be linked in particular to environmental variations (for example, a temperature gradient in the case of SPRi), cross-contamination, pollution of the electronic nose by so-called "poisonous" compounds, etc.

As the reference sensors are only sensitive to variations in physical parameters, the drift of the measuring system can be evaluated as the drift of the signal emitted by these reference sensors as illustrated by the bracket denoted A in FIG. 9. Since this drift also affects the detection sensors, it can be corrected by subtracting the signal emitted by a reference sensor from the signals emitted by the detection sensors.

As also mentioned above, sensor drift is the sum of the measuring system drift and the chemical sensor drift, caused for example by poisoning or progressive chemical pollution of the sensitive part of the sensor.

By following only the signal emitted by a given detection sensor, it is impossible to distinguish between these two sources of drift. On the other hand, the difference between the signal emitted by a detection sensor and that emitted by a reference sensor makes it possible to quantify the chemical drift, sensor by sensor, as illustrated by the brackets denoted B and C in FIG. 9.

Being able to determine the chemical drift of each detection sensor alone makes it possible to test the effectiveness of experimental solutions to reduce it as much as possible.

In this way, the electronic nose can be made more reliable and reproducible in the long term.

III—Properties of a Detection System According to the Invention with a Passivated Substrate III.1—Demonstration by Imagery of the Effect of Passivation on the Adsorption of VOCs on a Substrate:

The present test was carried out by passivating the surface of a substrate as described in Example II.1 above but having a different functionalization pattern from it (i.e. a different distribution of the detection and reference sensitive areas), using trifluoroethanethiol which, like 1H,1H,2H,2H-perfluorodecanethiol, is a compound with a perfluorinated alkyl group but with the shorter carbon chain (2 carbon atoms instead of 10).

This passivation has been achieved by diffusion of trifluoroethanethiol in the liquid phase onto the surface of the substrate.

This substrate was exposed to a gaseous sample comprising isoamyl butyrate under the same conditions as those described in Example II.1 above and the interactions between this VOC and the different sensitive areas of the substrate were monitored, again by SPRi.

Figure 10:
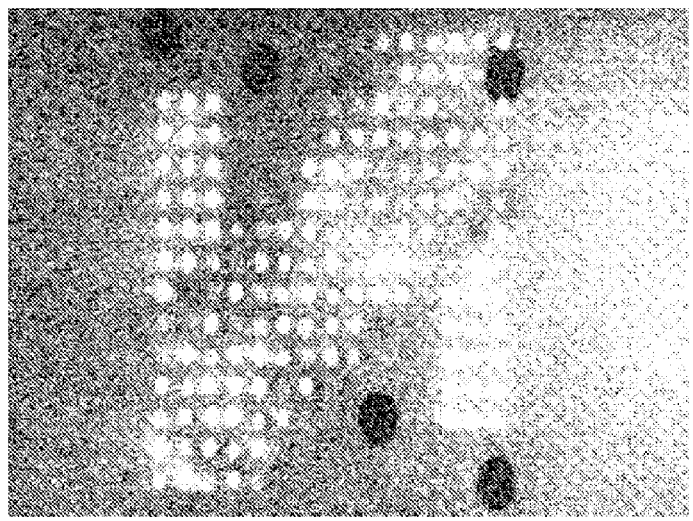
FIG. 10 is a differential image obtained by SPRi after exposure of a detection system according to the invention, having a passivated substrate, to a gaseous sample comprising isoamyl butyrate.

The differential image shown in FIG. 10 was thus obtained under the same contrast and brightness conditions as those used for the image in FIG. 4.

A comparison of these two images shows that the part of the surface of the substrate left free by the detection and reference sensitive areas appears darker in the image in FIG. 10, which means that the adsorption of isoamyl butyrate on this surface is reduced compared with that on the surface of a non-passivated substrate.

III.2—Reduction of the Chemical Drift of the Sensors:

A test was carried out by exposing successively:

on the one hand, a non-passivated substrate as described in Example II.1 above, to seven gaseous samples comprising, for the first two isoamyl butyrate (44.2 ppm and 37.1 ppm), for the third ethanol (173 ppm), for the fourth 1-octanol (4.2 ppm), for the fifth 1-propanol (192 ppm), for the sixth 1-butanol (75.6 ppm), and for the seventh isoamyl butyrate (40.6 ppm), and on the other hand, a passivated substrate as prepared in Example III.1 above, with six gaseous samples comprising, for the first two isoamyl butyrate (47.9 ppm and 53.2 ppm), for the third ethanol (168 ppm), for the fourth 1-octanol (3.8 ppm), for the fifth 1-propanol (165 ppm) and for the sixth 1-butanol (82.1 ppm), and this, over a period of 300 minutes and monitoring by SPRi and for each substrate, the change in reflectivity, % R, for a reference sensitive area, denoted R1, and for four detection sensitive areas, denoted D1 to D4, over this period.

The change in reflectivity was also monitored for an area of the gold layer, denoted Au, of the non-passivated substrate and for an area of the surface of the passivated substrate, denoted P1.

Figure 11A:
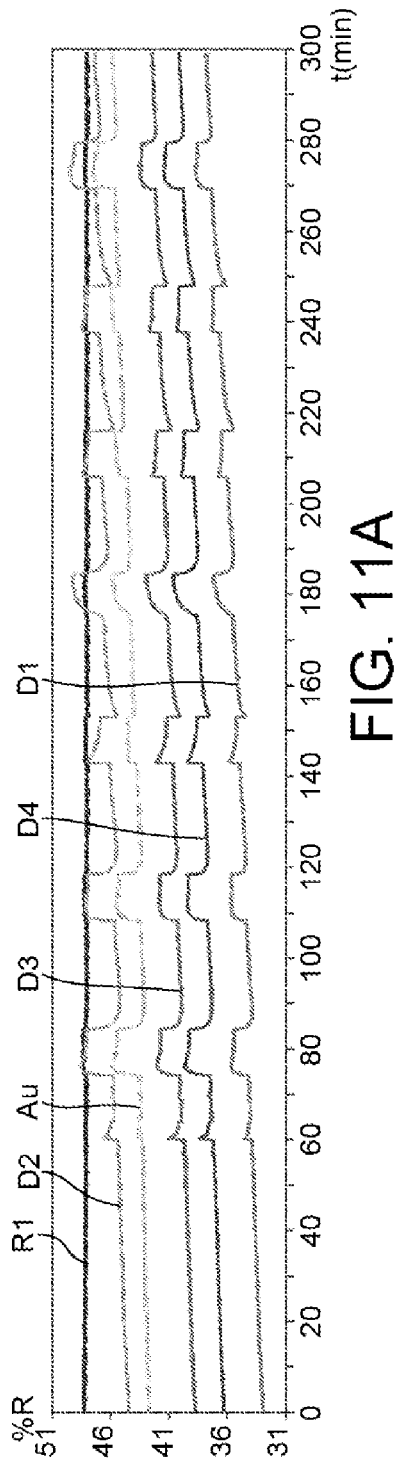
FIG. 11A shows the change in reflectivity, denoted % R, as a function of time, denoted t and expressed in minutes, as obtained by SPRi for four detection sensors (lines D1, D2, D3 and D4) and a reference sensor (line R1) of a detection system according to the invention, with a non-passivated substrate, over a period of 300 minutes during which these sensors were successively exposed to different gaseous samples each comprising a VOC; on this figure is also shown the change in reflectivity obtained for an area of the gold layer (line Au) forming the surface of the substrate.
Figure 11B:
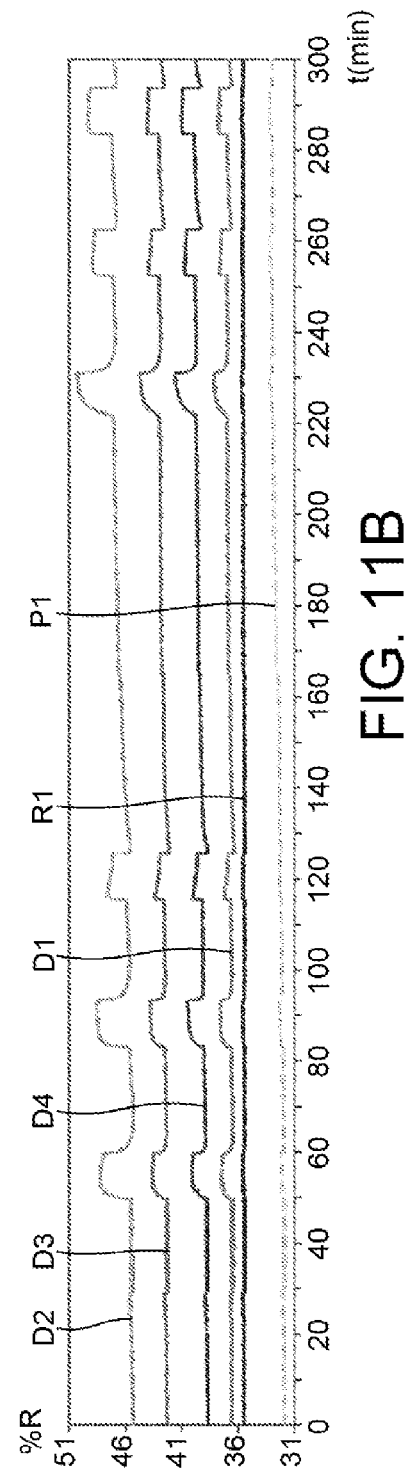
FIG. 11B is a figure analogous to that of FIG. 11A but for a detection system according to the invention, with a passivated substrate; this figure therefore does not include a line Au but includes a line P1 corresponding to the change in reflectivity obtained for an area of the surface of the passivated substrate.

FIGS. 11A and 11B were thus established, with FIG. 11A corresponding to the non-passivated substrate and FIG. 11B corresponding to the passivated substrate.

A comparison of these figures shows that passivation allows the reduction of the chemical drift for all the detection sensitive areas D1 to D4. Over 300 minutes (i.e. 5 hours) of analysis, the chemical drift can thus be halved from 0.6% $R \cdot h^{-1}$ (non-passivated substrate) to 0.3% $R \cdot h^{-1}$ (passivated substrate). For the analysis of a VOC over 10 minutes, the chemical drift obtained becomes of the order of the measurement noise, i.e. 0.05% R.

III.3—Resistance of the Detection System to a "Poison Effect":

Certain VOCs have a particular affinity for substrates covered with a layer of gold and their non-reversible attachment on this type of substrate can result in poisoning of the detection system, with a consequent decrease in the reliability and reproducibility of the detection provided by this system. For example, amines and thiols adsorb irreversibly to gold. However, these compounds can be targets of interest for certain applications, particularly in the food production industry in the case of amines.

Two tests were therefore carried out to check whether passivation of a substrate covered with a layer of gold could reduce the poisoning of this substrate.

The first test was carried out by exposing, on the one hand, a non-passivated substrate as described in Example II.1 above, and, on the other hand, a passivated substrate as prepared in Example III.1 above, to a gaseous sample comprising an amine, in this case amylamine ($CH_3(CH_2)_4NH_2$), for five minutes, after which the substrates were rinsed for 14 minutes under a stream of clean air.

The second test was carried out by exposing these same substrates to a series of three exposures to a gaseous sample comprising isoamyl butyrate. Between each exposure, amylamine was injected several times at a concentration ranging from 3 ppm to 50 ppm.

In both tests, the change in reflectivity, % R, was monitored by SPRi for a reference sensitive area, denoted R1, and for twenty-six detection sensitive areas, denoted D1 to D26. The change in reflectivity was also followed for an area of the gold layer, denoted Au, of the non-passivated substrate and for an area of the surface of the passivated substrate, denoted P1.

Figure 12A:
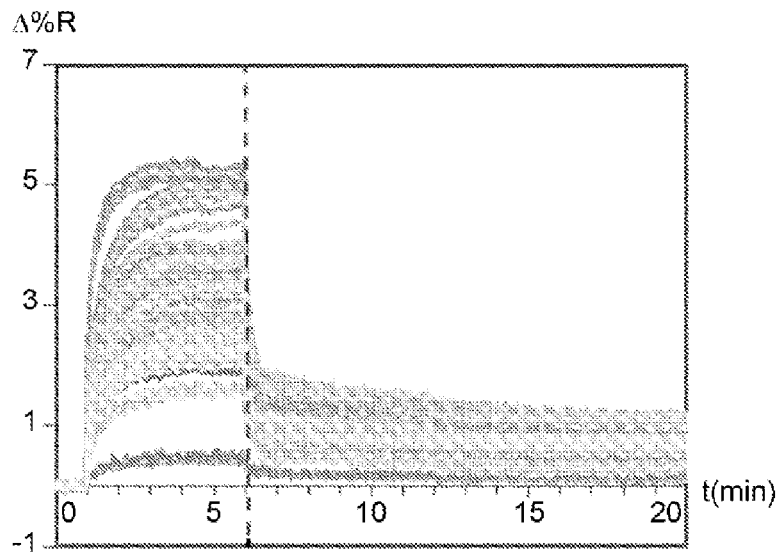
FIG. 12A illustrates the variation of the reflectivity, denoted $\Delta\% R$, as a function of time, denoted t and expressed in minutes, as obtained by SPRi for sensors of a detection system according to the invention, with a non-passivated substrate, during a 6-minute exposure to a gaseous sample comprising amylamine and then during a 14-minute rinsing of the substrate under a flow of clean air; in this figure, the vertical dotted line symbolizes the end of the exposure and the beginning of the rinsing.
Figure 12B:
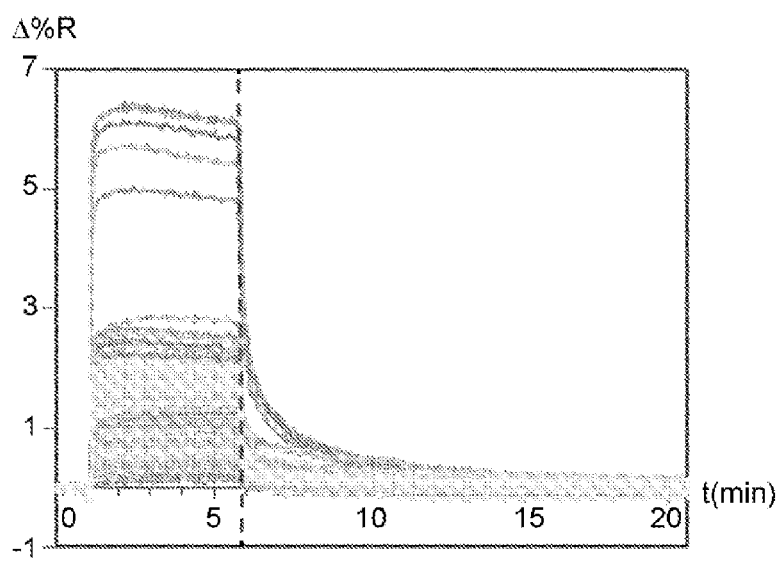
FIG. 12B is a figure analogous to FIG. 12A but for a detection system according to the invention, with a passivated substrate.
Figure 13A:
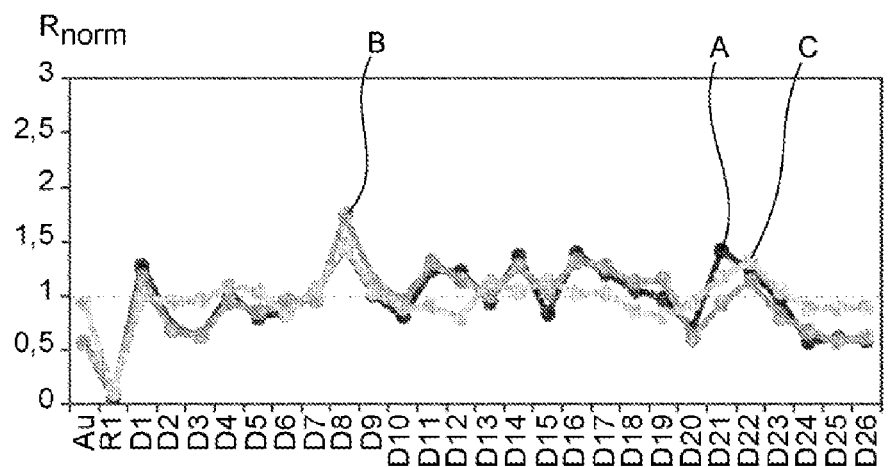
FIG. 13A shows the normalized reflectivity, denoted $R_{norm}$, as obtained by SPRi for twenty-six detection sensors, denoted D1 to D26, and for a reference sensor, denoted R1, of a detection system according to the invention, with a non-passivated substrate, for three exposures to a gaseous sample comprising isoamyl butyrate; between each exposure to isoamyl butyrate, amylamine was injected several times; on this figure is also shown the normalized reflectivity obtained for an area of the gold layer, denoted Au, forming the surface of the substrate; the points on the line A correspond to the normalized reflectivities obtained before the start of the amylamine injections; the points on the line B correspond to the normalized reflectivities obtained in the middle of the amylamine injections while the points on the curve C correspond to the normalized reflectivities obtained after the end of the amylamine injections.
Figure 13B:
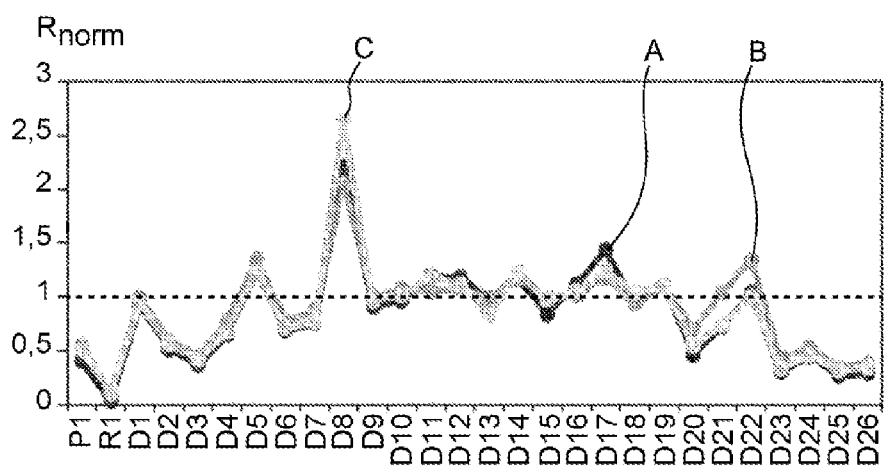
FIG. 13B is a figure analogous to FIG. 13A but for a detection system according to the invention, with a passivated substrate, and in which the normalized reflectivity shown for the area Au in FIG. 11A has therefore been replaced by that obtained for an area of the surface of the passivated substrate, denoted P1.

The results of the first test are illustrated, expressed in reflectivity variations ($\Delta\% R$), in FIGS. 12A and 12B, while the results of the second test are shown, expressed in normalized reflectivities ($R_{norm}$), in FIGS. 13A and 13B.

$$R_{norm} = \frac{\Delta\% R_D}{\Sigma_n \Delta\% R_{Dn}} \cdot N_D$$

where $\Delta\% R_D$ is the variation in reflectivity for a detection sensor D and $N_D$ the total number of detection sensors.

These figures show that, in the case of the non-passivated substrate (FIGS. 12A and 13A), the signals emitted by the majority of the sensors do not return to the baseline after rinsing the substrate under clean air flow. The amylamine has therefore become irreversibly bound under the experimental conditions.

On the other hand, in the case of the passivated substrate (FIGS. 12B and 13B), the return to the baseline is much better and therefore the irreversible attachment of the amylamine was limited.

FIGS. 13A and 13B also show an improvement in the repeatability of the detection system with passivation. Indeed, the profile obtained for isoamyl butyrate is maintained even after exposure to a poisonous compound such as amylamine.

III.4—Improvement of the Aging of the Detection System:

Two tests were therefore carried out to check whether passivation of a substrate covered with a gold layer could reduce the aging of the detection system.

The first test was performed by exposing, on the one hand, a non-passivated substrate as described in Example II.1 above, and, on the other hand, a passivated substrate as prepared in Example III.1 above, to gaseous samples comprising from 35 ppm to 55 ppm isoamyl butyrate, on the $6^{th}$ day (with 3 exposures), on the $14^{th}$ day (with 2 exposures) and on the $56^{th}$ day (with 2 exposures) of use for the first substrate and on the $9^{th}$ day (with 3 exposures), on the 15' day (with 2 exposures) and on the $61^{st}$ day (with 2 exposures) of use for the second substrate, and by monitoring by SPRi and for each substrate the change in reflectivity for a reference sensitive area, denoted R1, and for eighteen detection sensitive areas, denoted D1 to D18. The change in reflectivity was also monitored for an area of the gold layer, denoted Au, of the non-passivated substrate and for an area of the surface of the passivated substrate, denoted P1.

The second test was carried out by exposing:

a non-passivated substrate as described in Example II.1 above, hereinafter referred to as S1, a passivated substrate as prepared in Example III.1 above, i.e. passivated by liquid diffusion of trifluoroethanethiol, hereinafter referred to as S2, and a substrate prepared by passivating the surface of a substrate as described in Example II.1 above, by liquid diffusion of 1H,1H,2H,2H-perfluorodecanethiol, hereinafter referred to as S3, to gaseous samples comprising from 35 ppm to 55 ppm isoamyl butyrate, at 1 week, 2 months and 6 months of use of these substrates, and monitoring by SPRi and for each of the substrates S1, S2 and S3, the change in reflectivity for a reference sensitive area.

Figure 14A:
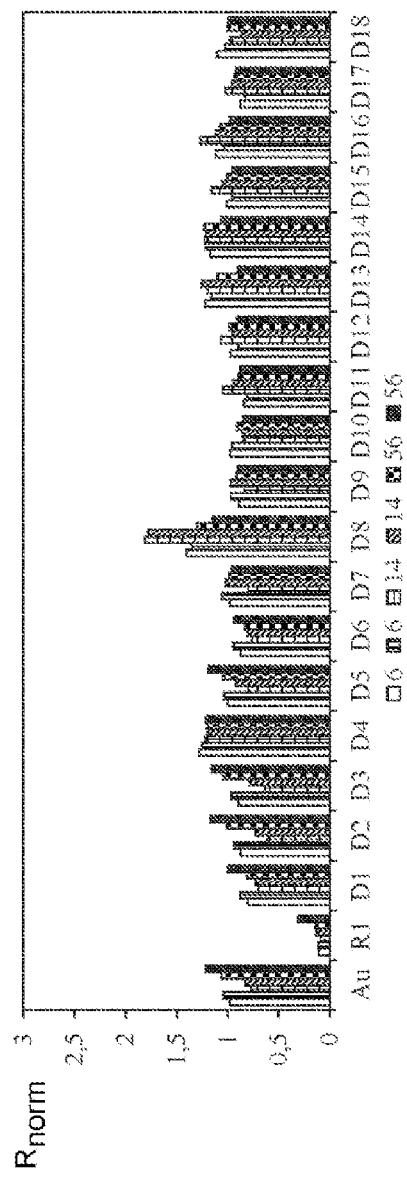
FIG. 14A shows the normalized reflectivity, denoted $R_{norm}$, as obtained by SPRi for eighteen detection sensors, denoted D1 to D18, and for a reference sensor, denoted R1, of a detection system according to the invention, with a non-passivated substrate, for exposures to a gaseous sample comprising isoamyl butyrate at 6, 14 and 56 days of use; also shown on this figure is the normalized reflectivity obtained for an area of the gold layer, denoted Au, forming the surface of the substrate.
Figure 14B:
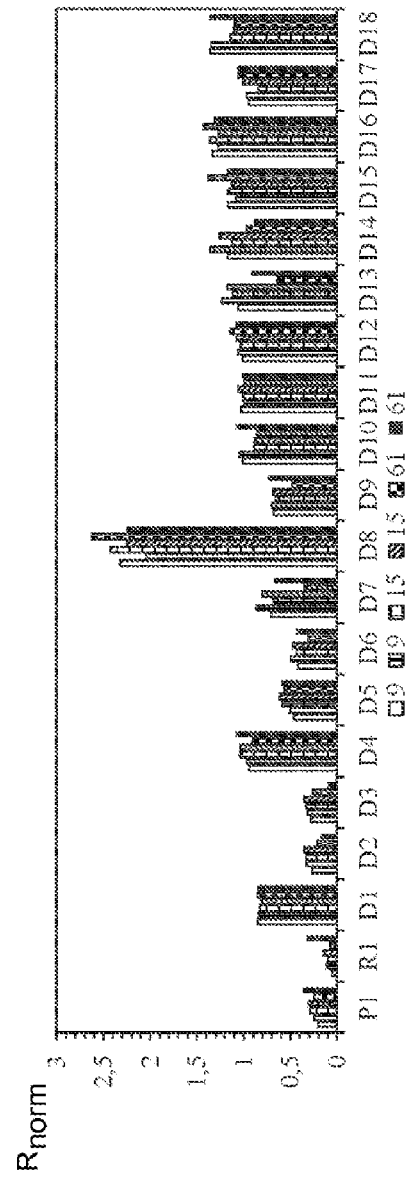
FIG. 14B is a figure analogous to FIG. 14A but for a detection system according to the invention, with a passivated substrate, having been exposed to a gaseous sample comprising isoamyl butyrate at 9, 15 and 61 days of use; in this figure, the normalized reflectivity shown for the area Au in FIG. 14A has therefore been replaced by that obtained for an area of the surface of the passivated substrate, denoted P1.
Figure 15:
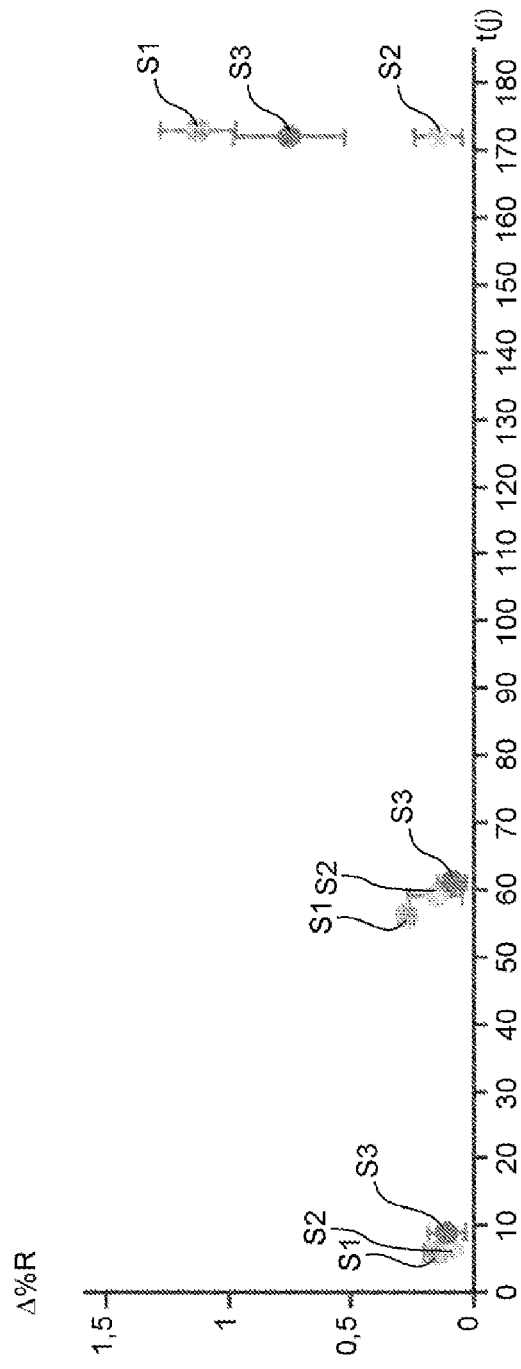
FIG. 15 shows the variation in reflectivity, denoted Δ% R, as a function of time, denoted t and expressed in days, as obtained by SPRi for a reference sensor of a detection system according to the invention, with a non-passivated substrate, denoted S1, and for a reference sensor of two detection systems according to the invention, with a passivated substrate, denoted S2 and S3, over a period of 180 days during which these sensors were successively exposed to three gaseous samples comprising isoamyl butyrate.

The results of the first test are illustrated, expressed in normalized reflectivities ($R_{norm}$), in FIGS. 14A and 14B, while the results of the second test are illustrated, expressed in variations of reflectivity ($\Delta\% R$), in FIG. 15.

FIGS. 14A and 14B show that, in the case of a non-passivated substrate (S1), the profile obtained on all the sensors deteriorates in time because the response of each sensor tends towards the same value. Thus, the ability of the electronics nose cone to differentiate between VOCs is lost. On the other hand, in the case of a passivated substrate (S2 and S3), the profile obtained on all the sensors is well preserved.

FIG. 15 shows that the insensitivity or very low sensitivity to VOCs of the reference sensors is also better preserved with a passivated substrate. By using trifluoroethanethiol as a passivating compound (S2), the reference sensors are even stabilized up to six months of use.

III.5—Reduction of Interference with Water Present in a Gaseous Sample:

The present test was performed using two substrates as described in Example II.1 above but with a different functionalization pattern from the example (i.e. a different distribution of the detection and reference sensitive areas).

The first substrate was not passivated while the second substrate was passivated with 1H,1H,2H,2H-perfluorohexanethiol.

This passivation was carried out by diffusion on the surface of the second substrate of 1H,1H,2H,2H-perfluorohexanethiol in the liquid phase at a concentration of 1 mmol/L in ethanol.

Each substrate was exposed to a gaseous sample comprising gasoline combustion gases from a gasoline vehicle exhaust.

The interactions between these combustion gases and the different sensitive areas of the two substrates were monitored by SPRi.

Since combustion products contain high levels of water vapor (approximately 70% relative humidity) because water is a combustion product of gasoline, these interactions were compared with those obtained for water vapor alone.

Figure 16A:
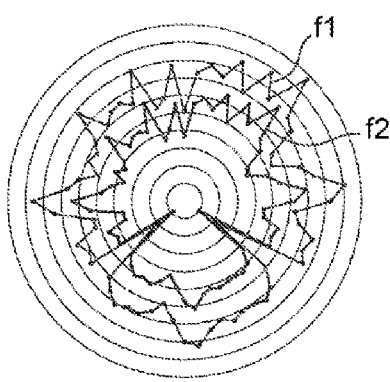
FIGS. 16A and 16B illustrate, in the form of spider web diagrams, the non-normalized (FIG. 16A) and normalized (FIG. 16B) signals as emitted by sensors of a detection system according to the invention, with a non-passivated substrate, following two different exposures: one to a gasoline combustion gas sample, the other to a water vapor sample; in these figures, the arrows f1 correspond to the signals emitted for the combustion gas sample while the arrows f2 correspond to the signals emitted for the water vapor sample.
Figure 16B:
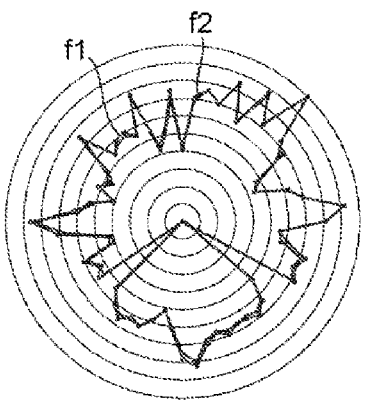
Figure 17A:
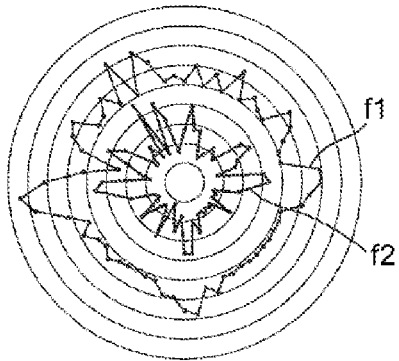
FIGS. 17A and 17B are figures analogous to FIGS. 16A and 16B but for a detection system according to the invention, with a passivated substrate; in these figures, the arrows f1 correspond to the signals emitted for the combustion gas sample while the arrows f2 correspond to the signals emitted for the water vapor sample.
Figure 17B:
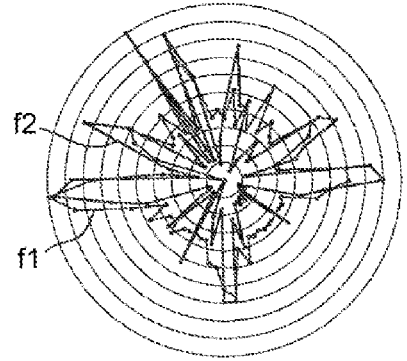

The results are shown, in the form of spider web diagrams (or radar diagrams), in FIGS. 16A and 16B for the non-passivated substrate and in FIGS. 17A and 17B for the passivated substrate. In these diagrams, each ray corresponds to the signal emitted by a sensitive area of the substrate, in absolute intensity for FIGS. 16A and 17A and in normalized intensity for FIGS. 16B and 17B. The arrows f1 correspond to the signals emitted for the gasoline combustion gas samples and the arrows f2 correspond to the signals emitted for the water vapor samples.

FIGS. 16A and 16B show that, for a non-passivated substrate, the signals due to the interactions of the sensitive areas of the substrate with the water vapor present in both types of sample almost completely cover the signals due to the interactions of these same sensitive areas with the combustion gases (approximately 260 ppm VOC) so that, in normalized data, the presence of the combustion gases is almost invisible (FIG. 16B).

In contrast, for a substrate passivated with a perfluorinated compound, the water vapor present in both types of sample generates a lower response from the sensitive areas and the results in normalized data are clearly different for the water vapor sample and the combustion gas sample (FIG. 17B). Signals due to combustion gas components other than water vapor are clearly visible and detectable.

This illustrates the ability of a perfluorinated coating, when used to passivate a substrate, to reduce interference with moisture which is present in many odorous samples often at much higher concentrations than those of the compounds being detected and identified.

REFERENCES CITED

[1] S. Brenet et al., *ISOCS/IEEE International Symposium on Olfaction and Electronic Nose (ISOEN), IEEE,* 2017, pp. 1-3
[2] Y. C. Lee et al., *19th International Conference on Solid-State Sensors, Actuators and Microsystems (Transducers), IEEE,* 2017, pp. 672-675
[3] *Handbook of Machine Olfaction: Electronic Nose Technology,* chapter 13, John Wiley & Sons 2006
[4] S. Di Carlo and M. Falasconi, *Drift correction methods for gas chemical sensors in artificial olfaction systems: techniques and challenges.* InTech: 2012
[5] K. Arshak, E. Moore, G. M. Lyons, J. Harris, and S. Clifford, *A review of gas sensors employed in electronic nose applications,* Sensor Review 2004, vol. 24, pp. 181-198
[6] T. Wasilewski, J. Gębicki, and W. Kamysz, *Bioelectronic nose: Current status and perspectives, Biosensors and Bioelectronics* 2017, vol. 87, pp. 480-494
[7] A. D. Wilson and M. Baietto, *Applications and Advances in Electronic-Nose Technologies, Sensors* (Basel) 2009, vol. 9, pp. 5099-5148

The invention claimed is:

1. A detection system for an electronic nose capable of detecting and identifying a set S of compounds likely to be present in a gaseous sample, the detection system comprising:
    a plurality of cross-reactive detection sensors for providing signals representative of the presence of one or more compounds of the set S in the gaseous sample, each detection sensor comprising at least one detection sensitive part;
    at least one reference sensor for providing a signal representative of the measurement noise of the detection system, the at least one reference sensor comprising at least one reference sensitive part;
    a substrate comprising a surface on which the at least one detection sensitive part and the at least one reference sensitive part are arranged, the surface further comprising:
        a plurality of detection sensitive areas, each of said detection sensitive areas corresponding to the detection sensitive part of one of the detection sensors and each of said detection sensitive areas comprising at least one detection receptor capable of interacting physicochemically with at least one compound of the set S of compounds; and
        at least one reference sensitive area which corresponds to the reference sensitive part of the reference sensor and which is functionalized with at least one first fluorinated compound selected from compounds of formula $C_vF_{2v+2}$ in which v is an integer ranging from 4 to 20, or compounds of formula $C_wF_{2w+1}$-$(L)_x$-Z in which w is an integer ranging from 1 to 12, x is 0 or 1, L represents a divalent spacer group while Z represents a group capable of allowing the at least one first fluorinated compound to be attached to the surface of the substrate.

2. The detection system as claimed in claim 1, wherein the surface of the substrate is a passivated surface.

3. The detection system as claimed in claim 2, wherein the surface of the substrate is passivated with a second fluorinated compound selected from compounds comprising at least one perfluorinated terminal alkyl group or fluorinated polymers, the second fluorinated compound being the same as or different than the at least one first fluorinated compound.

4. The detection system as claimed in claim 1, wherein the at least one first fluorinated compound is selected from compounds of formula $C_wF_{2w+1}$-$(L)_x$-Z in which w is an integer ranging from 1 to 12, x is 0 or 1, L represents a divalent spacer group while Z represents a group capable of allowing the at least one first fluorinated compound to be attached to the surface of the substrate.

5. The detection system as claimed in claim 4, wherein the divalent spacer group is a linear or branched, saturated or unsaturated hydrocarbon group comprising from 1 to 20 carbon atoms and optionally one or more heteroatoms.

6. The detection system as claimed in claim 5, wherein the divalent spacer group is a divalent alkylene group comprising from 1 to 20 carbon atoms.

7. The detection system as claimed in claim 5, wherein the divalent spacer group is a divalent alkylene group comprising from 1 to 12 carbon atoms.

8. The detection system as claimed in claim 4, wherein the at least one first fluorinated compound is a perfluoroalkanethiol of formula $CF_3(CF_2)_y(CH_2)_zSH$ in which y is an integer from 0 to 11 and z is an integer from 0 to 20.

9. The detection system as claimed in claim 8, wherein the at least one first fluorinated compound is 1H,1H-trifluoroethanethiol, 1H,1H,2H,2H-perfluoropentanethiol, 1H,1H,2H,2H-perfluorohexanethiol, 1H,1H,2H,2H-perfluorooctanethiol or 1H,1H,2H,2H-perfluorodecanethiol.

10. The detection system as claimed in claim 4, wherein the at least one first fluorinated compound is a perfluoroalkanethiol of formula $CF_3(CF_2)_y(CH_2)_zSH$ in which y is an integer from 0 to 11 and z is an integer from 1 to 12.

11. The detection system as claimed in claim 4, wherein the Z group is a thiol, amine, silanol, carbonyl or carboxyl group.

12. The detection system as claimed in claim 1, wherein the at least one first fluorinated compound is selected from polytetrafluoroethylenes, polyvinyl fluorides, polyvinylidene fluorides, perfluoroalkoxy alkanes, fluorinated ethylene-propylene copolymers or poly(ethylene-co-tetrafluoroethylene).

13. The detection system as claimed in claim 1, wherein the reference sensitive area is formed by a self-assembled layer of the at least one first fluorinated compound.

14. The detection system as claimed in claim 1, wherein the plurality of cross-reactive detection sensors and the at least one reference sensor are resistive, piezoelectric, mechanical, acoustic, and/or optical sensors.

15. The detection system as claimed in claim 14, wherein the plurality of cross-reactive detection sensors and the at least one reference sensor are optical surface plasmon resonance sensors.

16. An electronic nose capable of detecting and identifying a set S of compounds likely to be present in a gaseous sample, wherein the electronic nose comprises a detection system as defined in claim 1.

17. The electronic nose as claimed in claim 16, wherein the set S of compounds are volatile organic compounds.

18. The electronic nose as claimed in claim 17, wherein the volatile organic compounds are hydrogen sulfide and/or ammonia.

19. The detection system as claimed in claim 1, wherein the at least one first fluorinated compound is selected from compounds of formula $C_vF_{2v+2}$ in which v is an integer ranging from 4 to 20.

20. A detection system for detecting and identifying a set S of compounds in a gaseous sample, the detection system comprising:
 a plurality of cross-reactive detection sensors configured to provide a plurality of detection signals indicating presence of at least one member of the set S of compounds in the gaseous sample, each detection sensor comprising at least one detection sensitive part;
 at least one reference sensor providing at least one reference signal indicating measurement noise of the detection system, the at least one reference sensor comprising at least one reference sensitive part;
 a substrate comprising a passivated surface on which the at least one detection sensitive part and the at least one reference sensitive part are arranged, wherein the surface is passivated with at least one first fluorinated compound selected from compounds comprising at least one perfluorinated terminal alkyl group or fluorinated polymers, the passivated surface of the substrate further comprising
  at least one reference sensitive area functionalized with at least one second fluorinated compound selected from compounds of formula $C_vF_{2+2}$ in which v is an integer ranging from 4 to 20, or compounds of formula $C_wF_{2w+1}$-$(L)_x$-Z in which w is an integer ranging from 1 to 12, x is 0 or 1, L represents a divalent spacer group while Z represents a group capable of allowing the at least one second fluorinated compound to be attached to the surface of the substrate; and
 a plurality of detection sensitive areas having at least one detection receptor for physicochemically interacting with the at least one member of the set S of compounds.

21. The detection system of claim 20, wherein the surface is passivated with the at least one first fluorinated compound selected from compounds of formula $C_vF_{2+2}$ in which v is an integer ranging from 4 to 20, or compounds of formula $C_wF_{2w+1}$-$(L)_x$-Z in which w is an integer ranging from 1 to 12, x is 0 or 1, L represents a divalent spacer group while Z represents a group capable of allowing the at least one first fluorinated compound to be attached to the surface of the substrate.

* * * * *